(12) United States Patent
Mochizuki et al.

(10) Patent No.: US 11,576,370 B2
(45) Date of Patent: Feb. 14, 2023

(54) CHAMBER FOR TRANSPLANTATION, METHOD FOR MANUFACTURING CHAMBER FOR TRANSPLANTATION, DEVICE FOR TRANSPLANTATION, AND METHOD FOR FUSION WELDING POROUS MEMBRANES

(71) Applicant: FUJIFILM Corporation, Tokyo (JP)

(72) Inventors: Yusuke Mochizuki, Ashigarakami-gun (JP); Kuniyuki Kaminaga, Ashigarakami-gun (JP); Kazuhiro Hasegawa, Ashigarakami-gun (JP); Ryuta Takegami, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 543 days.

(21) Appl. No.: 16/728,529

(22) Filed: Dec. 27, 2019

(65) Prior Publication Data
US 2020/0138010 A1  May 7, 2020

Related U.S. Application Data

(63) Continuation of application No. PCT/JP2018/024670, filed on Jun. 28, 2018.

(30) Foreign Application Priority Data

Jun. 29, 2017  (JP) ............................. JP2017-127659

(51) Int. Cl.
*A01N 1/02* (2006.01)
*A61K 38/28* (2006.01)
(Continued)

(52) U.S. Cl.
CPC ........... *A01N 1/021* (2013.01); *A01N 1/0278* (2013.01); *A61K 38/28* (2013.01); *B01D 69/14* (2013.01);
(Continued)

(58) Field of Classification Search
None
See application file for complete search history.

(56) References Cited

U.S. PATENT DOCUMENTS

2004/0089600 A1* 5/2004 Haq ...................... B01D 53/78
210/337
2007/0237749 A1 10/2007 Wang
(Continued)

FOREIGN PATENT DOCUMENTS

CN  101466360 A  6/2009
CN  101528166 A  9/2009
(Continued)

OTHER PUBLICATIONS

Nyitray, Crystal E. et al., "Polycaprolacetone Thin-Film Micro- and Nanoporous Cell-Encapsulation Devices", ACS Nano, vol. 9, No. 6, 2015, pp. 5675-5682. (Year: 2015).*

(Continued)

*Primary Examiner* — Jason M Greene
(74) *Attorney, Agent, or Firm* — Birch, Stewart, Kolasch & Birch, LLP

(57) ABSTRACT

According to the present invention, there are provided a chamber for transplantation which has a high durability, and in which an enclosed biological constituent can be maintained for a long period of time because an interior space thereof is efficiently secured; and a method for manufacturing the chamber for transplantation. The chamber for transplantation includes one or more membranes for immunoisolation at a boundary between an inside and an outside of the chamber for transplantation, in which all of the membranes for immunoisolation include a porous membrane containing a polymer, and a joint portion at which the porous membranes are directly fusion welded to each other is provided. The method for manufacturing a chamber for transplantation includes preparing one or more porous membranes contain-
(Continued)

ing a polymer selected from polysulfone and polyethersulfone, bringing one part of the porous membrane into direct contact with another part of the porous membrane, and performing a heat fusion welding of the two parts that are in direct contact with each other at a temperature which is a glass transition temperature of the polymer or higher and lower than a melting point of the polymer.

19 Claims, 2 Drawing Sheets

(51) Int. Cl.
    *B01D 69/14* (2006.01)
    *B01D 71/68* (2006.01)

(52) U.S. Cl.
    CPC .......... *B01D 71/68* (2013.01); *B01D 2325/02* (2013.01); *B01D 2325/04* (2013.01); *B01D 2325/20* (2013.01)

(56) References Cited

U.S. PATENT DOCUMENTS

| | | | |
|---|---|---|---|
| 2010/0209468 A1 | 8/2010 | Kennedy et al. | |
| 2013/0026090 A1* | 1/2013 | Johnson | B01D 63/10 210/435 |
| 2016/0169645 A1* | 6/2016 | Emary | F42B 30/02 102/439 |
| 2016/0332119 A1 | 11/2016 | Fissell et al. | |
| 2017/0266626 A1 | 9/2017 | Kayama et al. | |
| 2018/0263238 A1* | 9/2018 | Flanagan | A01N 1/021 |
| 2018/0290110 A1* | 10/2018 | Hikita | B01D 71/80 |
| 2019/0262122 A1 | 8/2019 | Mochizuki et al. | |
| 2019/0262509 A1 | 8/2019 | Mochizuki et al. | |

FOREIGN PATENT DOCUMENTS

| | | |
|---|---|---|
| CN | 106573203 A | 4/2017 |
| CN | 109922839 A | 6/2019 |
| CN | 109982727 A | 7/2019 |
| WO | WO 92/07525 A1 | 5/1992 |
| WO | WO 97/17129 A1 | 5/1997 |
| WO | WO 2006/022358 A1 | 3/2006 |
| WO | WO 2018/088452 A1 | 5/2018 |

OTHER PUBLICATIONS

Petersen, P. et al., "Improved Diffusion Properties of a New Polysulfone Membrane for the Development of a Bioartifical Pancreas", Transplantation Proceedings, 33, 2001, pp. 1952-1953. (Year: 2001).*

Extended European Search Report, dated Apr. 8, 2020, for European Application No. 18824120.2.

Stamatialis et al., "Medical Applications of Membranes: Drug Delivery, Artificial Organs and Tissue Engineering," Journal of Membrane Science, vol. 308, No. 1-2, 2008 (Available online Oct. 3, 2007), pp. 1-34.

Barkai et al., Survival of encapsulated islets: More than a membrane story, World J Transplant, vol. 6, No. 1, Mar. 24, 2016, pp. 69-90.

International Preliminary Report on Patentability, dated Jan. 9, 2020, and Written Opinion of the International Searching Authority, dated Oct. 2, 2018, (Forms PCT/IB/326, PCT/IB/373 and PCT/ISA/237) for Application No. PCT/JP2018/024670, with English translation of the Written Opinion.

International Search Report (Form PCT/ISA/210) for International Application No. PCT/JP2018/024670, dated Oct. 2, 2018, with English translation.

Nyitray et al., "Polycaprolactone Thin-Film Micro- and Nanoporous Cell-Encapsulation Devices," ACS Nano, vol. 9, No. 6, 2015, pp. 5675-5682.

Petersen et al., "Improved Diffusion Properties of a New Polysulfone Membrane for the Development of a Bioartificial Pancreas," Transplantation Proceedings, vol. 33, 2001, pp. 1952-1953.

Rafael, "Cell Transplantation and Immunoisolation: Studies on a macroencapsulation device," Karolinska Institutet, Huddinge Hospital, 1999, pp. 1-83.

Tatarkiewicz et al., "Reversal of Hyperglycemia in Mice after Subcutaneous Transplantation of Macroencapsulated Islets," Transplantation, vol. 67, Issue 5, Mar. 15, 1999, pp. 665-671 (10 pages).

Japanese Office Action, dated Oct. 20, 2020, for Japanese Application No. 2019-527038, with an English translation.

Chinese Office Action and Search Report for Chinese Application No. 201880043616.3, dated Jun. 24, 2021, with English translation of the Office Action.

* cited by examiner

180°C

230°C

260°C

CHAMBER FOR TRANSPLANTATION, METHOD FOR MANUFACTURING CHAMBER FOR TRANSPLANTATION, DEVICE FOR TRANSPLANTATION, AND METHOD FOR FUSION WELDING POROUS MEMBRANES

CROSS-REFERENCE TO RELATED APPLICATIONS

This application is a continuation of PCT International Application No. PCT/JP2018/024670 filed on Jun. 28, 2018, which claims priority under 35 U.S.C § 119 (a) to Japanese Patent Application No. 2017-127659 filed on Jun. 29, 2017, the entire content of which is incorporated herein by reference.

BACKGROUND OF THE INVENTION

1. Field of the Invention

The present invention relates to a chamber for transplantation which includes a membrane for immunoisolation, and a method for manufacturing a chamber for transplantation. In addition, the present invention relates to a device for transplantation which includes the chamber for transplantation. The present invention further relates to a method for fusion welding porous membranes containing polysulfone or polyethersulfone.

2. Description of the Related Art

Immunoisolation is one of methods for preventing immune reactions in a recipient during transplantation of biological constituents such as cells, tissues, or organs. A membrane for immunoisolation is a selectively permeable membrane which allows water, oxygen, glucose, or the like to permeate, and which, at the same time, performs immunoisolation by inhibiting permeation of immune cells and the like involved in an immune rejection. For example, while preventing an immune rejection, it is possible to achieve a purpose of transplantation by a device for transplantation utilizing a membrane for immunoisolation which allows physiologically active substances to permeate therethrough, for transplantation of cells secreting the physiologically active substances.

Transplantation, 67, 665 (1999) discloses that transplantation is performed using a commercially available chamber for transplantation (TheraCyte (registered trade name)), the chamber being formed by using a porous membrane that is a laminate membrane obtained by laminating a membrane having a pore diameter of 0.45 µm and cell retention properties and an outer membrane of polytetrafluoroethylene (PTFE) having a pore diameter of 5 µm. The chamber for transplantation has a structure in which two sheets of the laminate membranes are joined to each other by sandwiching a polyester film at an end portion in which surfaces of membranes having a pore diameter of 0.45 µm and cell retention properties overlap each other so that they face each other (Cell transplantation and immunoisolation Studies on macroencapsulation by Elab Rafael, B.Sc., M.D. (ISBN 91-628-3883-0)).

SUMMARY OF THE INVENTION

In the chambers for transplantation disclosed in Transplantation, 67, 665 (1999) and Cell transplantation and immunoisolation Studies on macroencapsulation by Elab Rafael, B.Sc., M.D. (ISBN 91-628-3883-0), a joint portion is easily peeled off due to autoclaving treatment or dry-heat sterilization treatment. In addition, in a case of incorporating pancreatic β cells to observe insulin secretion, insulin secretion that does not correspond to an external glucose concentration may be observed, or the cells may die because a shape of a mass of the incorporated pancreatic β cells collapses.

Furthermore, because the membrane for immunoisolation used in the chambers for transplantation disclosed in Transplantation, 67, 665 (1999) and Cell transplantation and immunoisolation Studies on macroencapsulation by Elab Rafael, B.Sc., M.D. (ISBN 91-628-3883-0) is a multi-layered laminate, costs easily increase.

An object of the present invention is to provide a chamber for transplantation which has a high durability, and in which an enclosed biological constituent can be maintained for a long period of time because an interior space thereof is efficiently secured. In addition, another object of the present invention is to provide a chamber for transplantation which can be manufactured at low cost.

The inventors of the present invention have assumed that the above-mentioned peeling of the joint portion occurs based on a difference in coefficient of linear expansion between the membrane for immunoisolation and the polyester film. In addition, the inventors of the present invention have considered that the problems occurring at the time of incorporating pancreatic β cells are caused because the polyester film, which is inserted for joining, protrudes into the inside of the chamber for transplantation and unnecessarily stimulates enclosed biological constituents.

Based on the above-mentioned considerations, the inventors of the present invention have conducted intensive studies to join membranes for immunoisolation without intervening other layers, have obtained a chamber for transplantation having a structure in which membranes for immunoisolation are directly fusion welded to each other at a joint portion, and therefore have completed the present invention.

That is, the present invention provides the following <1> to <17>.

<1> A chamber for transplantation, comprising:
one or more membranes for immunoisolation at a boundary between an inside and an outside of the chamber for transplantation,
in which all of the membranes for immunoisolation include a porous membrane containing a polymer, and
a joint portion at which the porous membranes are directly fusion welded to each other is provided.

<2> The chamber for transplantation according to <1>, in which different end portions of one porous membrane are directly fusion welded to each other at the joint portion.

<3> The chamber for transplantation according to <1> or <2>, in which end portions of two porous membranes are directly fusion welded to each other at the joint portion.

<4> The chamber for transplantation according to any one of <1> to <3>, in which a width of the joint portion is 0.1 mm to 1.5 mm.

<5> The chamber for transplantation according to any one of <1> to <4>, in which all of the porous membranes contain polysulfone or polyethersulfone.

<6> The chamber for transplantation according to any one of <1> to <5>, in which the porous membrane has, in the inside thereof, a layered compact portion where a pore diameter is the smallest.

<7> The chamber for transplantation according to <6>, in which the pore diameter continuously increases in a thickness direction from the compact portion toward at least one surface of the porous membrane.

<8> The chamber for transplantation according to <6> or <7>, in which the compact portion is present close to any one surface X from a central portion in thickness of the porous membrane.

<9> The chamber for transplantation according to <8>, in which the surface X is on the inside.

<10> A device for transplantation, comprising the chamber for transplantation according to any one of <1> to <9> enclosing a biological constituent therein.

<11> The device for transplantation according to <10>, in which the biological constituent releases a physiologically active substance.

<12> The device for transplantation according to <11>, in which the physiologically active substance is insulin.

<13> A method for manufacturing a chamber for transplantation having one or more membranes for immunoisolation at a boundary between an inside and an outside, the method comprising:

preparing one or more porous membranes containing a polymer selected from polysulfone and polyethersulfone;

bringing one part of the porous membrane into direct contact with another part of the porous membrane; and performing a heat fusion welding of the two parts that are in direct contact with each other at a temperature which is a glass transition temperature of the polymer or higher and lower than a melting point of the polymer.

<14> The manufacturing method according to <13>, in which the heat fusion welding is performed at 230° or higher and lower than 340° C.

<15> The manufacturing method according to <13> or <14>, further comprising, bringing different end portions of one porous membrane into direct contact with each other.

<16> The manufacturing method according to any one of <13> to <15>, further comprising, bringing end portions of two porous membranes into direct contact with each other.

<17> A method for directly fusion welding porous membranes to each other which contain a polymer selected from polysulfone and polyethersulfone, in which the fusion welding is performed by heating the porous membranes at 230° C. or higher and lower than 340° C.

According to the present invention, it is possible to provide a chamber for transplantation which has a high durability, and in which an enclosed biological constituent can be maintained for a long period of time because an interior space thereof is efficiently secured. For example, by using a porous membrane containing polysulfone or polyethersulfone, it is possible to provide a chamber for transplantation which can be manufactured at low cost. The present invention further provides a method for fusion welding porous membranes containing polysulfone or polyethersulfone.

DESCRIPTION OF THE PREFERRED EMBODIMENTS

Hereinafter, the present invention will be described in detail.

In the present specification, "to" is used to refer to a meaning including numerical values denoted before and after "to" as a lower limit value and an upper limit value.

<<Chamber for Transplantation>>

A chamber for transplantation is a container for transplanting a biological constituent into a recipient. The chamber for transplantation can enclose the biological constituent therein.

Figure 1:
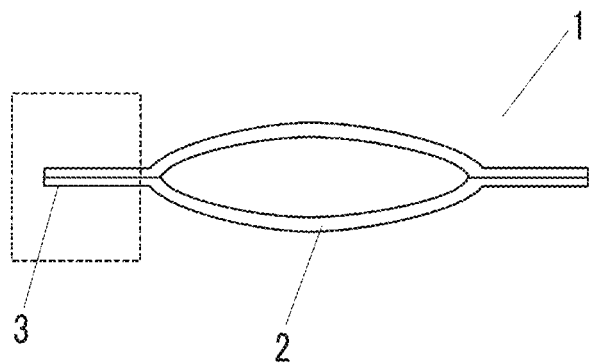
FIG. 1 is a cross-sectional schematic view showing an example of a chamber for transplantation of the present invention.

The chamber for transplantation according to the embodiment of the present invention has one or more membranes for immunoisolation in a boundary between the inside and the outside of the chamber for transplantation. The membrane for immunoisolation includes a porous membrane containing a polymer. FIG. 1 shows a cross-sectional schematic view of an example of the chamber for transplantation according to the embodiment of the present invention. In the example shown in FIG. 1, a chamber for transplantation 1 forming a joint portion 3 by directly fusion welding end portions of two porous membranes to each other and having an inside for enclosing a biological constituent is obtained.

<Membrane for Immunoisolation>

In the present specification, a membrane for immunoisolation refers to a membrane used for immunoisolation.

Immunoisolation is one of a method for preventing an immune rejection by a recipient in a case of transplantation. Here, the immune rejection is a rejection by a recipient with respect to a biological constituent to be transplanted. A biological constituent is isolated from an immune rejection by a recipient due to immunoisolation. Examples of immune rejections include reactions based on cellular immune responses and reactions based on humoral immune responses.

The membrane for immunoisolation is a selectively permeable membrane that allows nutrients such as oxygen, water, and glucose to permeate therethrough, and inhibits permeation of immune cells and the like involved in an immune rejection. Examples of immune cells include macrophages, dendritic cells, neutrophils, eosinophils, basophils, natural killer cells, various T cells, B cells, and other lymphocytes.

Depending on the application, the membrane for immunoisolation preferably inhibits permeation of high-molecular-weight proteins such as immunoglobulins (IgM, IgG; and the like) and complements, and preferably allows a relatively low-molecular-weight physiologically active substances such as insulin to permeate therethrough.

The selective permeability of the membrane for immunoisolation may be adjusted according to the application. The membrane for immunoisolation may be a selectively permeable membrane which blocks a substance having a molecular weight such as 500 kDa or more, 100 kDa or more, 80 kDa or more, or 50 kDa or more. For example, it is preferable that the membrane for immunoisolation be capable of inhibiting permeation of the smallest IgG (molecular weight of about 160 kDa) among antibodies. In addition, the membrane for immunoisolation may be a selectively permeable membrane which blocks a substance having a diameter such as 500 nm or more, 100 nm or more, 50 nm or more, or 10 nm or more, as a sphere size.

The chamber for transplantation according to the embodiment of the present invention includes one or more membranes for immunoisolation in a boundary between the inside and the outside of the chamber for transplantation. The membrane for immunoisolation may be formed of only the porous membrane or may contain other layers such as a hydrogel membrane.

A thickness of the membrane for immunoisolation is not particularly limited, but may be 1 μm to 500 μm, is preferably 10 μm to 300 μm, and is more preferably 15 μm to 250 μm.

The membrane for immunoisolation is disposed at at least a part of the boundary (a boundary that separates the inside and the outside) between the inside and the outside of the chamber for transplantation. By disposing in such a manner, it is possible to protect the biological constituent enclosed in the chamber for transplantation from immune cells and the like present outside, and to introduce nutrients such as water, oxygen, and glucose into the inside of the chamber for transplantation from the outside.

The membrane for immunoisolation may be disposed on the entire surface of a boundary between the inside and the outside of the chamber for transplantation, and may be disposed a part of the surface corresponding to an area of, for example, 1% to 99%, 5% to 90%, 10% to 80%, 20% to 70%, 30% to 60%, 40% to 50%, or the like with respect to the entire area. The membrane for immunoisolation is preferably disposed on substantially the entire surface of the boundary between the inside and the outside of the chamber for transplantation. A surface on which the membrane for immunoisolation is disposed may be one continuous portion or may be divided into two or more portions.

In a case where the membrane for immunoisolation is not disposed on the entire surface of the boundary between the inside and the outside of the chamber for transplantation, it is sufficient that a remaining surface is formed of an impermeable membrane not allowing permeation of nutrients such as oxygen, water, and glucose, in addition to cells and the like.

[Porous Membrane]
(Structure of Porous Membrane)

The porous membrane is a membrane having a plurality of pores. Pores can be confirmed by, for example, captured images of a scanning electron microscope (SEM) or captured images of a transmission electron microscope (TEM) of a cross section of the membrane.

A thickness of the porous membrane is not particularly limited, but may be 1 μm to 250 μm, is preferably 10 μm to 220 μm, and is more preferably 15 μm to 200 μm.

In the membrane for immunoisolation, the porous membrane preferably has a layered compact portion where a pore diameter is the smallest within the inside. In addition, it is preferable that a pore diameter continuously increase in the thickness direction from the compact portion toward at least one of the surfaces of the porous membrane. The pore diameter is determined by an average pore diameter of a parting line which will be described later.

The surface of the membrane means a main surface (a front surface or a back surface showing an area of the membrane), and does not mean a surface in the thickness direction of an end of the membrane. The surface of the porous membrane may be an interface with another layer. In the membrane for immunoisolation, it is preferable that the porous membrane have the same structure in an intra-membrane direction (a direction parallel to the membrane surface) with respect to pore diameters or pore diameter distribution (a difference in pore diameters in the thickness direction).

With the porous membrane having pore diameter distribution in the thickness direction, the life of the chamber for transplantation according to the embodiment of the present invention can be improved. The reason is that, by using a plurality of membranes having substantially different pore diameters, effects are obtained as though multistage filtration would be carried out, and therefore a deterioration in the membrane can be prevented.

A pore diameter may be measured from a photograph of a cross section of the membrane obtained by an electron microscope. The porous membrane can be cut with a microtome or the like, and it is possible to obtain a photograph of a cross section of the porous membrane as a section of a thin membrane which a cross section can be observed.

In the present specification, the comparison of pore diameters in the thickness direction of the membrane is performed by comparing pore diameters in 19 parting lines in a case where an SEM image of the cross section of the membrane is divided into 20 in the thickness direction of the membrane. 50 or more consecutive pores that intersect or are in contact with the parting line are selected, each of the pore diameters is measured, and an average value is calculated as an average pore diameter. Here, as the pore diameter, not a length of a portion where the selected pore intersects the parting line, but a diameter is used, the diameter being calculated using an area, which is obtained by calculating an area of pores calculated from an SEM image of the cross section of the membrane by image processing, as an area of a true circle. In this case, for a parting line in which pores are large and therefore only up to 50 pores can be selected, an average pore diameter is assumed to an average pore diameter obtained by measuring 50 pores by broadening the field of view of an SEM image for obtaining the cross section of the membrane. Pore diameters in the thickness direction of the membrane are compared by comparing the obtained average pore diameter for each parting line.

The layered compact portion having the smallest pore diameter refers to a layered portion of the porous membrane including the parting line where an average pore diameter becomes the smallest among parting lines in a photograph of the cross section of the membrane. The compact portion may include two or more parting lines. For example, in a case where two or more parting lines, which have an average pore diameter 1.1 times or less the minimum average pore diameter, are consecutive, the compact portion is assumed to include two or more consecutive parting lines. In the present specification, a thickness of the compact portion is a product of the number of parting lines included in the compact portion and one-twentieth of the thickness of the membrane.

A thickness of the compact portion may be 0.5 μm to 50 μm, and is preferably 0.5 μm to 30 μm. In the present specification, an average pore diameter of the compact portion is denoted as the minimum pore diameter of the porous membrane. The minimum pore diameter of the porous membrane is preferably 0.02 μm to 1.5 μm, and is more preferably 0.02 μm to 1.3 μm. The reason is that the minimum pore diameter of such a porous membrane can inhibit permeation of at least normal cells. An average pore diameter of the compact portion is measured by ASTM F316-80.

The porous membrane preferably has the compact portion within the inside. The phrase "within the inside" means that the compact portion is not in contact with the surface of the membrane. The phrase "having the compact portion within the inside" means that the compact portion is not a portion that contains the parting line closest to any surface of the membrane. By using the porous membrane having a structure having the compact portion within the inside, permeability of a substance intended to permeate is unlikely to lower compared to a case of using a porous membrane having the compact portion, which is in contact with the surface thereof. Although not bound by any theory, it is perceived that protein adsorption is less likely to occur due to the presence of the compact portion within the inside.

It is preferable that the compact portion be biased to one of the front surface side than a central portion in thickness of the porous membrane. Specifically, the compact portion is preferably located between any one surface of the porous membrane and a portion at a distance of less than half the thickness of the porous membrane from the surface, and it is even more preferably located between any one surface of the porous membrane and a portion at a distance of two-fifths the of the porous membrane from the surface. This distance may be determined from the photograph of the cross section of the membrane described above. In the present specification, the surface of the porous membrane closer to the compact portion is referred to as a "surface X."

In a case the porous membrane has the surface X, it is preferable in the chamber for transplantation that the surface X of the porous membrane be on the inside thereof. That is, it is preferable that the membrane for immunoisolation be disposed so that the compact portion of the porous membrane in the membrane for immunoisolation is closer to the inside of the chamber for transplantation. By setting the surface X in the inside of the chamber for transplantation, it is possible to make permeability of physiologically active substances higher.

In the porous membrane, it is preferable that a pore diameter continuously increase in the thickness direction from the compact portion toward at least one of the surfaces. In the porous membrane, the pore diameter may continuously increase in the thickness direction toward the surface X from the compact portion, the pore diameter may continuously increase in the thickness direction toward the surface opposite to the surface X from the compact portion, and the pore diameter may continuously increase in the thickness direction toward any surface of the porous membrane from the compact portion. Among them, it is preferable that the pore diameter continuously increase in the thickness direction toward at least the surface opposite to the surface X from the compact portion, and it is preferable that the pore diameter continuously increase in the thickness direction toward any surface of the porous membrane from the compact portion. The sentence "the pore diameter continuously increases in the thickness direction" means that a difference in average pore diameters between the abovementioned parting lines adjacent to each other in the thickness direction increases by 50% or less of a difference between maximum average pore diameters (maximum pore diameter) and minimum average pore diameters (minimum pore diameter), preferably increase by 40% or less, and more preferably increase by 30% or less. The phrase "continuously increasing" essentially means that a pore diameter increases uniformly without decreasing, but a decreasing portion may occur accidentally. For example, in a case of combining two parting lines from the surface, in a case where an average value of a combination increases uniformly (uniformly decreases toward the compact portion from the surface), it can be determined that "the pore diameter continuously increases in the thickness direction toward the surface of the membrane from the compact portion."

A structure of the porous membrane in which a pore diameter continuously increases in the thickness direction can be realized by, for example, a manufacturing method to be described later.

A maximum pore diameter of the porous membrane is preferably more than 1.5 µm and 25 µm or less, is more preferably 1.8 µm to 23 µm, and is even more preferably 2.0 µm to 21 µm. In the present specification, an average pore diameter of the parting line having the maximum average pore diameter among the parting lines of the cross section of the membrane is referred to as the maximum pore diameter of the porous membrane.

A ratio of an average pore diameter of the compact portion to the maximum pore diameter of the porous membrane (a ratio of a minimum pore diameter to a maximum pore diameter of the porous membrane, which is a value obtained by dividing the maximum pore diameter by the minimum pore diameter, an "anisotropy ratio" in the present specification) is preferably 3 or more, is more preferably 4 or more, and is even more preferably 5 or more. The reason is that an average pore diameter except for that of the compact portion increases to increase substance permeability of the porous membrane. In addition, the anisotropy ratio is preferably 25 or less, and is more preferably 20 or less. The reason is that effects, as though multistage filtration would be carried out, can be efficiently obtained within a range where an anisotropy ratio is 25 or less.

It is preferable that a parting line with a maximum average pore diameter be a parting line closest to any surface of the membrane or a parting line in contact with that parting line.

In the parting line closest to any surface of the membrane, it is preferable that an average pore diameter be more than 0.05 µm and 25 µm or less, be more preferably more than 0.08 µm and 23 µm or less, and be even more preferably more than 0.5 µm and 21 µm or less. In addition, a ratio of an average pore diameter of the compact portion to an average pore diameter of the parting line closest to any surface of the membrane is preferably 1.2 to 20, is more preferably 1.5 to 15, and is even more preferably 2 to 13.

(Elemental Distribution of Porous Membrane)

Formulas (I) and (II) are preferably satisfied for at least one surface of the porous membrane.

$$B/A \leq 0.7 \qquad (I)$$

$$A \geq 0.015 \qquad (II)$$

In the formula, A represents a ratio of an N element (nitrogen atom) to a C element (carbon atom) on a surface of the membrane, and B represents a ratio of the N element to the C element at a depth of 30 nm from the same surface.

Formula (II) shows that a certain amount or more of N element is present on at least one surface of the porous membrane, and Formula (I) shows that an N element in the porous membrane is localized at a depth of less than 30 nm of the surface.

With the surface satisfying Formulas (I) and (II), a bioaffinity of the porous membrane, particularly, a bioaffinity of the surface side satisfying Formulas (I) and (II) becomes high.

In the porous membrane, either one of surfaces may satisfy Formulas (I) and (II), or both surfaces may satisfy Formulas (I) and (II), but it is preferable that both surfaces satisfy Formulas (I) and (II). In a case where either one of surfaces satisfies Formulas (I) and (II), the surface thereof may be in an inside or an outside of a chamber for transplantation to be described later, but the surface is preferably in the inside thereof. In addition, in a case where only one of any surface satisfies Formulas (I) and (II) and the porous membrane has the above-mentioned surface X, a surface satisfying Formulas (I) and (II) is preferably the surface X.

In the present specification, a ratio (A value) of N element to C element on the membrane surface and a ratio (B value) of N element to C element at a depth of 30 nm from the surface are obtained by calculating using X-ray photoelectron spectroscopy (XPS) measurement results. The XPS measurement is X-ray photoelectron spectroscopy, which is a method for irradiating a membrane surface with X-rays, measuring kinetic energy of photoelectrons emitted from the membrane surface, and analyzing a composition of elements constituting the membrane surface. Under conditions using a monochromated Al—Kα ray described in Examples, the A value is calculated from results at the start of sputtering, and the B value is calculated from time results, which are calculated that the ray is at 30 nm from the surface of the membrane measured from a sputtering rate.

B/A may be 0.02 or more, and is preferably 0.03 or more, and is more preferably 0.05 or more.

A is preferably 0.050 or more, and is more preferably 0.080 or more. In addition, A may be 0.20 or less, and is preferably 0.15 or less, and is more preferably 0.10 or less.

B may be 0.001 to 0.10, and is preferably 0.002 to 0.08, and is more preferably 0.003 to 0.07.

In a method for manufacturing the porous membrane which will be described later, the elemental distribution of the porous membrane, especially the distribution of an N element, can be controlled by a moisture concentration contained in the temperature-controlled humid air, a time to apply the temperature-controlled humid air, a temperature of a coagulation liquid, an immersion time, a temperature of a diethylene glycol bath for washing, an immersion time in the diethylene glycol bath for washing, a speed of a porous membrane manufacture line, and the like. The distribution of the N element can also be controlled by an amount of moisture contained in a stock solution for forming a membrane.

(Composition of Porous Membrane)

The porous membrane contains a polymer. It is preferable that the porous membrane be substantially composed of a polymer.

The polymer forming the porous membrane is preferably biocompatible. Here, the term "biocompatible" means that the polymer has non-toxic and non-allergenic properties, but does not have properties such that the polymer is encapsulated in a living body.

The number average molecular weight (Mn) of the polymer is preferably 1,000 to 10,000,000, and is more preferably 5,000 to 1,000,000.

Examples of polymers include thermoplastic or thermosetting polymers. Specific examples of polymers include polysulfone, cellulose acylate such as cellulose acetate, nitrocellulose, sulfonated polysulfone, polyethersulfone, polyacrylonitrile, styrene-acrylonitrile copolymer, styrene-butadiene copolymer, saponified ethylene-vinyl acetate copolymer, polyvinyl alcohol, polycarbonate, an organosiloxane-polycarbonate copolymer, a polyester carbonate, an organopolysiloxane, a polyphenylene oxide, a polyamide, a polyimide, polyamideimide, polybenzimidazole, ethylene vinyl alcohol copolymer, polytetrafluoroethylene (PTFE), and the like. From the viewpoints of solubility, optical physical properties, electrical physical properties, strength, elasticity, and the like, polymers may be homopolymers, copolymers, polymer blends, or polymer alloys.

Among them, polysulfone, polyethersulfone, and cellulose acylate are preferable, and polysulfone is more preferable.

In a case where polysulfone or polyethersulfone is used as the polymer, the porous membrane preferably further contains a hydrophilic polymer. Examples of hydrophilic polymers include polyvinylpyrrolidone, hydroxypropyl cellulose, hydroxyethyl cellulose, and the like. Among them, polyvinylpyrrolidone is preferable. By combining polysulfone or polyethersulfone which are hydrophobic with the hydrophilic polymer, biocompatibility can be improved.

The porous membrane may contain other components other than the above-mentioned components as an additive.

Examples of additives include metal salts of inorganic acids such as sodium chloride, lithium chloride, sodium nitrate, potassium nitrate, sodium sulfate, and zinc chloride; metal salts of organic acids such as sodium acetate and sodium formate; other polymers such as polyethylene glycol; high polymer electrolytes such as sodium polystyrene sulfonate and polyvinyl benzyl trimethyl ammonium chloride; ionic surfactants such as sodium dioctyl sulfosuccinate and sodium alkyl sodium taurate; and the like. The additive may act as a swelling agent for a porous structure. As an additive, it is preferable to use a metal salt. The porous membrane containing polysulfone or polyethersulfone preferably contains lithium chloride.

The porous membrane is preferably a membrane formed from a single composition as a single layer, and preferably not has a laminated structure of a plurality of layers.

(Method for Manufacturing Porous Membrane)

A method for manufacturing the porous membrane is not particularly limited as long as the method can form the porous membrane having the above structure, and any general methods for forming a polymer membrane can be used. Examples of methods for forming a polymer membrane include a stretching method, a flow-casting method, and the like, and a flow-casting method is preferable.

For example, in the flow-casting method, it is possible to produce a porous membrane having the above-mentioned structure by adjusting the type and amount of a solvent used in a stock solution for forming a membrane, and a drying method after flow casting.

Manufacture of a porous membrane by using a flow-casting method can be carried out by a method including, for example, the following (1) to (4) in this order.

(1) A stock solution for forming a membrane, which contains a polymer, if necessary an additive and, if necessary a solvent, is flow-cast on a support while being in a dissolved state.

(2) The surface of the flow-cast liquid membrane is exposed to temperature-controlled humid air.

(3) The membrane obtained after being exposed to temperature-controlled humid air is immersed in a coagulation liquid.

(4) A support is peeled off if necessary.

A temperature of temperature-controlled humid air may be 4° C. to 60° C., and is preferably 10° C. to 40° C. A relative humidity of the temperature-controlled humid air may be 15% to 100%, and is preferably 25% to 95%. The temperature-controlled humid air may be applied at a wind speed of 0.1 m/s to 10 m/s for 0.1 seconds to 30 seconds, preferably 1 second to 10 seconds.

In addition, an average pore diameter and position of the compact portion can also be controlled by a moisture concentration contained in the temperature-controlled humid air and a time of applying the temperature-controlled humid air. An average pore diameter of the compact portion can also be controlled by an amount of moisture contained in a stock solution for forming a membrane.

By applying the temperature-controlled humid air to the surface of the liquid membrane as described above, it is possible to cause coacervation from the surface of the liquid membrane toward the inside by controlling evaporation of a solvent. By immersing the membrane in a coagulation liquid containing a solvent having low solubility of the polymer but compatible with the solvent of the polymer in this state, the above-mentioned coacervation phase is fixed as fine pores, and pores other than the fine pores can also be formed.

A temperature of the coagulation liquid may be −10° C. to 80° C. in a process of immersing the membrane in the coagulation liquid. By changing a temperature during this period, it is possible to control a size of a pore diameter up to a support surface side by adjusting a time from the formation of the coacervation phase on the support surface side to the solidification from the compact portion. In a case where a temperature of the coagulation liquid is raised, the formation of the coacervation phase becomes faster and a time for solidification becomes longer, and therefore the pore diameter toward the support surface side tends to become large. On the other hand, in a case where a temperature of the coagulation liquid is lowered, the formation of the coacervation phase becomes slower and a time for solidification becomes shorter, and therefore the pore diameter toward the support surface side is unlikely to become large.

As the support, a plastic film or a glass plate may be used. Examples of materials of the plastic film include polyester such as polyethylene terephthalate (PET), polycarbonate, acrylic resin, epoxy resin, polyurethane, polyamide, polyolefin, a cellulose derivative, silicone, and the like. As the support, a glass plate or PET is preferable, and PET is more preferable.

The stock solution for forming a membrane may contain a solvent. A solvent having high solubility of the polymer to be used (hereinafter referred to as "favorable solvent") may be used depending on a polymer to be used. As a favorable solvent, it is preferable that the solvent be quickly substituted with the coagulation liquid in a case where the membrane is immersed in the coagulation liquid. Examples of solvents include N-methyl-2-pyrrolidone, dioxane, tetrahydrofuran, dimethylformamide, dimethylacetamide, or a mixed solvent thereof in a case where the polymer is polysulfone and the like; dioxane, N-methyl-2-pyrrolidone, dimethylformamide, dimethylacetamide, dimethylsulfoxide, or a mixed solvent thereof in a case where the polymer is polyacrylonitrile and the like; dimethylformamide, dimethylacetamide, or a mixed solvent thereof in a case where the polymer is polyamide and the like; acetone, dioxane, tetrahydrofuran, N-methyl-2-pyrrolidone, or a mixed solvent thereof in a case where the polymer is cellulose acetate and the like. Among them, N-methyl-2-pyrrolidone is preferably used.

In addition to a favorable solvent, the stock solution for forming a membrane preferably use a solvent (hereinafter referred to as "non-solvent") in which the solubility of the polymer is low but is compatible with the solvent of the polymer. Examples of non-solvents include water, cellosolves, methanol, ethanol, propanol, acetone, tetrahydrofuran, polyethylene glycol, glycerin, and the like. Among these, it is preferable to use water.

A concentration of the polymer as the stock solution for forming a membrane may be 5 mass % to 35 mass %, is preferably 10 mass % to 30 mass %. By setting the concentration thereof to 35 mass % or less, sufficient permeability (for example, water permeability) can be imparted to the obtained porous membrane. By setting the concentration thereof to 5 mass % or more, the formation of a porous membrane which selectively allows substances to permeate can be secured. An amount of additive to be added is not particularly limited as long as the homogeneity of the stock solution for forming a membrane is not lost by the addition, but is 0.5% by volume to 10% by volume respect to a general solvent. In a case where the stock solution for forming a membrane contains a non-solvent and a favorable solvent, a ratio of the non-solvent to the favorable solvent is not particularly limited as long as a mixed solution can be maintained in a homogeneous state, but is preferably 1.0 mass % to 50 mass %, is more preferably 2.0 mass % to 30 mass %, and is even more preferably 3.0 mass % to 10 mass %.

In addition, in the stock solution for forming a membrane for manufacturing a porous membrane containing a polymer selected from the group consisting of polysulfone and polyethersulfone, and containing polyvinylpyrrolidone, polyvinylpyrrolidone is preferably contained by an amount of 50 mass % to 120 mass %, and more preferably by an amount of 80 mass % to 110 mass %, with respect to a total mass of polysulfone and polyethersulfone. Furthermore, in a case where the stock solution for forming a membrane contains lithium chloride as an additive, lithium chloride is preferably contained by an amount of 5 mass % to 20 mass %, and more preferably by 10 mass % to 15 mass %, with respect to the total mass of polysulfone and polyethersulfone.

As the coagulation liquid, it is preferable to use a solvent having a low solubility of the polymer used. Examples of such solvents include water, alcohols such as methanol, ethanol, and butanol; glycols such as ethylene glycol and diethylene glycol; aliphatic hydrocarbons such as ether, n-hexane, and n-heptane; glycerol such as glycerin; and the like. Examples of preferred coagulation liquids include water, alcohols, or a mixture of two or more of these. Among these, it is preferable to use water.

After immersion in the coagulation liquid, it is also preferable to perform washing with a solvent different from the coagulation liquid that has been used. Washing can be carried out by immersing in a solvent. Diethylene glycol is preferable as a washing solvent. Distribution of an N element in the porous membrane can be adjusted by adjusting either or both of a temperature and an immersion time of diethylene glycol in which a film is immersed by using diethylene glycol as a washing solvent. In particular, in a case where polyvinylpyrrolidone is used as the stock solution for forming a membrane of the porous membrane, a residual amount of polyvinylpyrrolidone on the membrane can be controlled. After washing with diethylene glycol, furthermore, the membrane may be washed with water.

Regarding a method for manufacturing the porous membrane, reference can be made to JP1992-349927A (JP-H04-349927A), JP1992-068966B (JP-H04-068966B), JP1992-351645A (JP-H04-351645A), JP2010-235808A, and the like.

[Other Layers]

The membrane for immunoisolation may contain layers other than the porous membrane. However, it is preferable that at least one surface of the membrane for immunoisolation be the porous membrane. This is to enable porous membranes to be directly fusion welded at the joint portion.

Examples of other layers include a hydrogel membrane. As a hydrogel membrane, a biocompatible hydrogel membrane is preferable. Examples thereof include an alginic acid gel membrane, an agarose gel membrane, a polyisopropyl acrylamide membrane, a membrane containing cellulose, a membrane containing a cellulose derivative (for example, methyl cellulose), a polyvinyl alcohol membrane, or the like. The hydrogel membrane is preferably an alginic acid gel membrane. Specific examples of alginic acid gel membranes include a polyion complex membrane of alginic acid-poly-L-lysine-alginic acid.

<Joint Portion>

Figure 2:
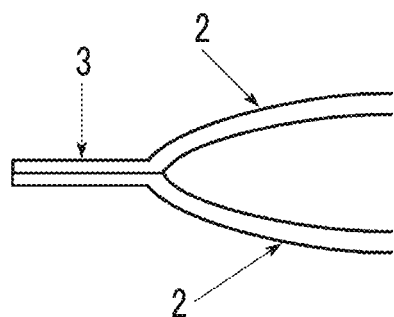
FIG. 2 is a cross-sectional schematic view showing a portion including a joint portion of an example of the chamber for transplantation of the present invention.
Figure 3:
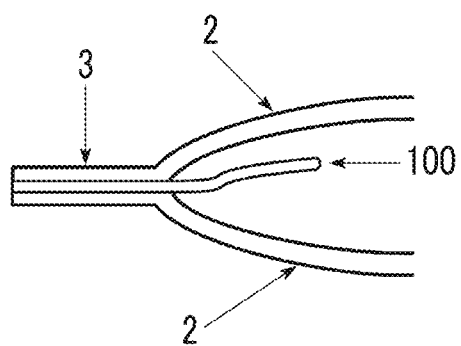
FIG. 3 is a cross-sectional schematic view showing a portion including a joint portion of an example of a chamber for transplantation of the related art.

The chamber for transplantation according to the embodiment of the present invention has a joint portion at which the membranes for immunoisolation are joined to each other. Porous membranes are directly fusion welded to each other at the joint portion. In each porous membrane, not the whole, but a part of a portion directly involves the direct fusion welding and becomes a joint portion. As described above, in the related art, end portions of two membranes for immunoisolation are fusion welded to each other through a thermoplastic resin layer such as a polyester film to form a chamber. Whereas, in the chamber for transplantation according to the embodiment of the present invention, porous membranes are directly fusion welded to each other. With such a structure, the chamber for transplantation according to the embodiment of the present invention does not have problems derived from a stimulation or the like by the thermoplastic resin layer which is formed of a different material from that of the porous membrane. In addition, as schematically shown in FIG. 3, in the chamber for transplantation in which the porous membranes are joined to each other through the thermoplastic resin layer, there is a problem of unnecessary stimulations to enclosed biological constituents or difficulties in securing an interior space because a thermoplastic resin layer 100 protrudes into the inside of the chamber for transplantation and becomes a protrusion portion. On the other hand, as schematically shown in FIG. 2, in the chamber for transplantation according to the embodiment of the present invention, a protrusion portion which causes such a problem is not formed.

It is sufficient for the porous membranes to have substantially the same composition in a thickness direction of the joint portion through direct fusion welding of the porous membranes to each other, and thereby integrating portions of the porous membranes. The phrase "be directly fusion welded" means that two membranes are fusion welded to each other in a state of coming in direct contact with each other by not sandwiching another material therebetween. It is preferable that the fusion welding be a heat fusion welding.

The inventors of the present invention have found that porous membranes containing a polymer selected from the group consisting of polysulfone and polyethersulfone are directly fusion welded to each other to be integrated by heating the porous membranes at a temperature which is a glass transition temperature of the polymer or higher and lower than a melting point of the polymer. For example, a glass transition temperature of polysulfone is 190° C., and porous membranes containing polysulfone can be directly fusion welded to each other by heating them at 190° C. or higher.

Usually, fusion welding of a polymer requires heating above its melting point, but it is also suggested for the porous membranes containing polysulfone or polyethersulfone to be directly fusion welded according to collapse of pores.

In a case of using the porous membrane containing a polymer selected from the group consisting of polysulfone and polyethersulfone, specifically, it is sufficient for heating for the fusion welding to be performed at 190° C. or higher and lower than 340° C., and it is preferably performed at 230° C. or higher and lower than 340° C.

Whether or not two porous membranes are directly fusion welded can be determined using, for example, cross-sectional SEM images as shown in Examples. In a case where no vacancy is observed, two porous membranes can be determined to be directly fusion welded to each other. Specifically, the determination is made based on porosity. In a case where a porosity is 20% or less, preferably approximately 5% or less, two porous membranes can be determined to be directly fusion welded to each other. A porosity can be obtained by tracing vacancies in the cross-sectional SEM image of the joint portion with a digitizer, obtaining a total area of all vacancies in the cross section, and calculating a ratio of the total area thereof to a cross-sectional area of the entire membrane.

In addition, directly fusion welding of two porous membranes can also be determined by analyzing the cross section with Raman spectrum. In Raman shift derived from a polymer forming the porous membrane, in a case where a joint portion fragment obtained by cutting with a microtome or the like is scanned in a thickness direction of the joint portion, and a certain strength or more is observed in the thickness direction of the joint portion fragment, it can be determined that two porous membranes are directly fusion welded. For example, scanning can be performed at 1600 $cm^{-1}$ derived from Ph expansion in a microscopic Raman spectrum using a 100 times objective lens (xy resolution: 1 mm) in an excitation wavelength of 785 nm. As an apparatus, for example, Nanofinder 30 manufactured by Tokyo Instruments, Inc. can be used.

It is preferable that the joint portion be formed by directly fusion welding end portions of the porous membrane. By directly fusion welding at the end portions, it is possible to obtain a chamber for transplantation having an inside with a large volume which is obtained by maximally utilizing an area of the porous membrane. For example, it is preferable that end portions of two porous membranes be directly fusion welded to each other, or different end portions of one porous membrane be directly fusion welded to each other. The end portions are substantially the entire periphery of the porous membrane. For example, it is preferable that end portions be directly fusion welded to each other over the entire outer periphery of two porous membranes of which outer peripheries can overlap each other. In addition, it is also preferable that one porous membrane having a line symmetric structure be folded into two, and end portions be directly fusion welded to each other over the entire outer peripheries facing each other. However, in any case, the joint portion preferably includes an injection port or the like for injecting biological constituents or the like into the chamber for transplantation, and this portion may not be directly fusion welded.

In the present specification, in a case where the term "end portion" is used regarding the porous membrane, it means a peripheral portion or a part thereof having a constant width which is substantially in contact with the side surface (edge) of the porous membrane thickness.

Same as the membrane for immunoisolation, the joint portion inhibits permeation of immune cells and the like involved in an immune rejection. In addition, in the joint portion, selective permeability of the membrane for immunoisolation allowing permeation of nutrients such as oxygen, water, and glucose may be maintained, but it may not be maintained, and the joint portion may be impermeable to not allow permeation of nutrients such as oxygen, water, and glucose.

A width of the joint portion is preferably 0.1 mm to 1.5 mm, and is more preferably 0.3 mm to 1.3 mm. The width of the joint portion is a length in a normal direction of an outer periphery direction of a directly fusion welded portion in a case where end portions of a porous membrane are directly fusion welded, for example.

<Structure and the Like of Chamber for Transplantation>

A shape of the chamber for transplantation is not limited, and may be a shape such as a pouched-like shape, a bag shape, a tube shape, or a microcapsule shape. A shape of the chamber for transplantation is preferably a shape capable of preventing movement of the chamber for transplantation within a recipient in a case where the chamber for transplantation is used as a device for transplantation to be described later. Specific examples of shapes of the chamber for transplantation include a cylindrical shape, a disk-like shape, a rectangular shape, an egg shape, a star shape, a circular shape, and the like. The chamber for transplantation may be in a form of a sheet, a strand, a spiral, or the like. The chamber for transplantation may be a chamber for transplantation which encloses the biological constituent and becomes the above-described shape only in a case where the chamber for transplantation used as a device for transplantation to be described later. It is preferable that the chamber for transplantation according to the embodiment of the present invention have the above forms or shape by directly fusion welding and combining one, two, or three or more parts consisting of the membrane for immunoisolation as described above.

The chamber for transplantation may contain a biocompatible plastic or the like for maintaining the shape and strength as a container. For example, the boundary between the inside and the outside of the chamber for transplantation may be formed from a porous membrane and a biocompatible plastic. In addition, in the chamber for transplantation of which the porous membrane is disposed on the entire surface of the boundary between the inside and the outside, a biocompatible plastic having a net-like structure may be further disposed on the outside of the boundary between the inside and the outside, from the viewpoint of strength.

<Injection Port>

The chamber for transplantation preferably includes an injection port or the like for injecting the biological constituent or the like into the chamber for transplantation. As the injection port, a tube leading to the inside of the chamber for transplantation may be provided.

The tube may contain a thermoplastic resin, for example. The thermoplastic resin preferably has a melting point which is lower than that of the polymer material of the porous membrane.

Specific examples of thermoplastic resins used in the tube include polyethylene, polypropylene, polyurethane, polyvinyl chloride, polytetrafluoroethylene, polyethylene terephthalate, and polycarbonate. Among them, polyethylene, polypropylene, polyurethane, polyvinyl chloride, and polytetrafluoroethylene are preferable, and polyethylene, polyurethane, and polyvinyl chloride are particularly preferable.

For example, the tube is sandwiched between the membranes for immunoisolation in a manner of coming into contact with a part of the porous membrane, and thereby joining with the part thereof. Joining can be performed by fusion welding, adhesion using an adhesive, and the like.

Among them, it is preferable to perform fusion welding. The fusion welding may be heat fusion welding.

In a case of performing fusion welding, the tube preferably contains a thermoplastic resin having a melting point which is lower than that of the polymer material of the porous membrane. The reason is that, in a case of performing fusion welding between the porous membrane and a tube containing a thermoplastic resin having a melting point which is lower than that of the polymer material of the porous membrane, the tube material is considered to be first melted at the time of heating so that the melted tube material can get into the pores of the porous membrane.

In a case of performing adhesion, the adhesive can be appropriately selected according to the polymer constituting the membrane or the material of the tube, and epoxy-based adhesives, silicone-based adhesives, acrylic-based adhesives, urethane-based adhesives, and the like can be used as the adhesive. For example, in a case where a tube containing a resin material having a melting point lower than that of the polymer material of the porous membrane is used, joining can be performed by adhesion.

<Application of Chamber for Transplantation>

The chamber for transplantation encloses the biological constituent and is used for transplantation of the biological constituent into the recipient. By using the chamber for transplantation, it is possible to prevent an immune rejection by the recipient with respect to the transplanted biological constituent. That is, the membrane for immunoisolation can be used for protecting biological constituents from an immune system of a recipient. In the present specification, a recipient means a living body to which transplantation is performed. A recipient is preferably a mammal, and is more preferably a human.

[Biological Constituent]

The biological constituent means a structure body derived from a living body. Examples of living bodies include viruses, bacteria, yeasts, fungal cells, insects, plants, mammals, and the like. It is preferable that a living body be generally a mammal. Examples of mammals include bovines, swine, sheep, cats, dogs, humans, and the like. The biological constituent is preferably a structure body derived from any of mammals.

Examples of biological constituents include organs, tissues, cells, and the like. Among these, cells are preferable as biological constituents. As cells, a single cell may be used or a plurality of cells may be used. It is preferable that a plurality of cells be used. A plurality of cells may be separated from each other or may be an aggregate.

The biological constituent may be obtained directly from a living body. In addition, particularly in a case where the biological constituent is a cell, the biological constituent may be directly obtained from a living body, or may be obtained by differentiation-induction of cells such as embryonic stem cells (ES cell), induced pluripotent stem cells (iPS cell), and mesenchymal stem cells. The cell may be a progenitor cell.

As a biological constituent, as one aspect, it is preferable to release a physiologically active substance. Examples of physiologically active substances include various hormones, various cytokines, various enzymes, and various other biologic factors in a living body. More specific examples include insulin, dopamine, factor VIII, and the like.

Here, insulin is a polypeptide (molecular weight of about 6000) in which an A chain of 21 amino acid residues and a B chain of 30 amino acid residues are linked via a disulfide bond. In insulin in a living body of a mammal is secreted from β cells in pancreatic islets of Langerhans. In a case of using insulin-secreting cells as the biological constituent in the present invention, insulin secreted may be human-type insulin or other mammalian-type (for example, porcine-type) insulin. Insulin may be insulin produced by a genetic recombination method. As a method for obtaining genetically modified insulin, for example, the description of Kadowaki Takashita: Diabetes Navigator (refer to 270-271, Takeo Tao, Yoshikazu Oka "Insulin Preparations of Present and Future," Medical Review, 2002) can be referred to. Various types of insulin analogues (refer to, for example, H. C. Lee, J. W. Yoon, et al., Nature, 408, 483-488, 2000) may be used.

The biological constituent is preferably an insulin-secreting cell. Insulin-secreting cells are cells that can secrete insulin in response to changes in blood glucose level. The insulin-secreting cells are not particularly limited. Examples thereof include pancreatic β cells present in pancreatic islets of Langerhans. Pancreatic β cells may be human pancreatic β cells, or may be pancreatic β cells such as pigs and mice. For a method for extracting pancreatic β cells from a pig, reference can be made to the description in JP2007-195573A. In addition, the insulin-secreting cells may be cells derived from human stem cells (refer to, for example, Junichi Miyazaki, Regenerative Medicine, Vol. 1, No. 2, pp. 57-61, 2002), or cells derived from small intestinal epithelial stem cells (refer to, for example, Fumikomi Mineko et al., Regenerative Medicine, Volume 1, No. 2, pp. 63 to 68, 2002), or insulin-secretory cells into which a gene encoding insulin has been incorporated (refer to, for example, H. C. Lee, J. W. Yoon, et al., Nature, 408, pp. 483-488, 2000). Furthermore, the insulin-secreting cells may be pancreatic islets of Langerhans (refer to, for example, Horiyama, Kazumori Inoue, Regenerative Medicine, Volume 1, No. 2, pp. 69 to 77, 2002).

<<Device for Transplantation>>

The device for transplantation is a complex including at least a chamber for transplantation and a biological constituent. In the device for transplantation, the chamber for transplantation encloses the biological constituent therein.

In the device for transplantation, the chamber for transplantation may enclose only the biological constituent therein, or may enclose the biological constituent, and constituents or components other than the biological constituent therein. For example, the biological constituent may be enclosed in the chamber for transplantation together with a hydrogel, and preferably in a state of being enclosed in the hydrogel. In addition, the device for transplantation may contain pH buffers, inorganic salts, organic solvents, proteins such as albumin, or peptides.

The device for transplantation may contain only one biological constituent or may contain two or more biological constituents. For example, the device for transplantation may contain only a biological constituent which releases physiologically active substances for the purpose of transplantation, or which serves other functions of transplantation; or may further contain a biological constituent assisting functions of these biological constituents.

The device for transplantation may be, for example, a device to be transplanted intraperitoneally or subcutaneously. In addition, the device for transplantation may be a blood-vessel-connecting device. For example, in a case where insulin-secreting cells are used as the biological constituent, insulin secretion corresponding to a change in blood glucose level becomes possible by performing transplantation such that blood and a membrane come into direct contact with each other.

Regarding the device for transplantation and chamber for transplantation, the description of Protein Nucleic Acid Enzyme, Vol. 45, pp. 2307 to 2312, (Okawara Hisako, 2000), JP2009-522269A, JP1994-507412A (JP-H06-507412A), and the like can be referred to.

EXAMPLES

Characteristics of the present invention will be described in more detail with reference to the following examples and comparative examples. The materials, amounts used, proportions, treatment details, treatment procedures, and the like disclosed in the following Examples can be modified as appropriate as long as the gist of the present invention is maintained. Therefore, the scope of the present invention should not be limitedly interpreted by the specific examples described below.

Examples 1 to 7, Comparative Example 7

[Production of Polysulfone Porous Membrane]

15 parts by mass of polysulfone (P3500 manufactured by Solvay), 15 parts by mass of polyvinylpyrrolidone (K-30), 1 part by mass of lithium chloride, and 2 parts by mass of water were dissolved in 67 parts by mass of N-methyl-2-pyrrolidone. Thereby, a stock solution for forming a membrane was obtained. This stock solution for forming a membrane was flow-cast on a surface of a PET film by a thickness of 200 μm. The flow-cast membrane surface was exposed to air adjusted to 25° C. and relative humidity 80% RH, at 2 m/sec for 5 seconds. Immediately thereafter, the exposed membrane surface was immersed in a coagulation liquid tank filled with water. The PET film was peeled off, and therefore a porous membrane was obtained. Thereafter, the immersed membrane surface was put into a diethylene glycol bath at 80° C. for 120 seconds, and then was thoroughly washed with pure water.

SEM imaging (S-5200, Hitachi High-Technologies Corporation, 10.0 kV) of a cross section of the obtained porous membrane was performed. As a result of an image analysis, the obtained porous membrane had a pore diameter distribution in which a pore diameter continuously increased in a thickness direction toward a surface, and had a compact portion within an inside. A thickness of the porous membrane was 50 μm, the minimum pore diameter was 0.8 μm, and the maximum pore diameter was 5.6 μm. The compact portion was located at a point of 20 μm from one surface (surface X), and was a surface on a side to which air was applied during the manufacture.

[Production of Chamber for Transplantation]

The produced polysulfone porous membrane was cut into 3 cm×5 cm. In Examples 1 to 5 and Comparative Example 7, the cut polysulfone porous membrane was folded into two such that a surface to which air was applied during the manufacture became an inner side. In Example 7, the cut polysulfone porous membrane was folded into two such that a surface to which air was applied during the manufacture became an outer side. In Example 6, the cut polysulfone porous membrane was further cut in half (parallel to a short side of 3 cm), and a side to which air was applied during the manufacture and the opposite side thereof of the two sections were allowed to face each other. Thereafter, using a sealer for tea bag (T-230K) manufactured by FUJIIMPULSE CO., LTD., a total of three sides of two long sides and one short side of a 3 cm×2.5 cm rectangle were heated at the temperature shown in the table. The temperature was measured by a thermocouple. Thereafter, the remaining one side was inserted in a state where a metal rod was inserted into Intramedic polyethylene tube (PE200), and in this state, both were respectively heated at the same temperature using the same sealer. Thereafter, a surrounding portion was cut with a knife so that a width thereof became a width of the table. Thereby, a chamber for transplantation having a size of 1 cm×2 cm was produced.

Figure 4:
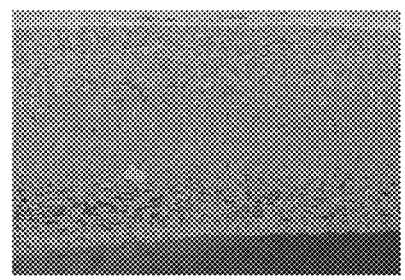
FIG. 4 is a view showing cross-sectional SEM images of joint portions of chambers for transplantation in Comparative Example 7, Example 1, and Example 2.
Figure 4:
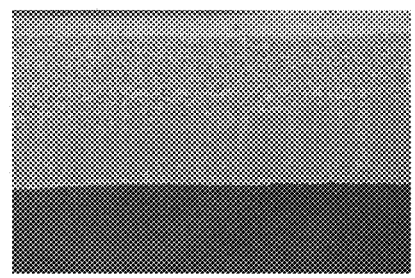
Figure 4:
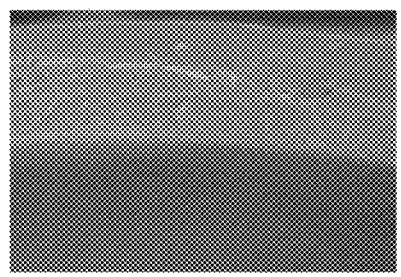

FIG. 4 shows cross-sectional SEM images of heated portions (joint portions) of chambers for transplantation in Comparative Example 7 (180° C.), Example 1 (230° C.), and Example 2 (260° C.). In Comparative Example 7, a vacancy was observed, and it could be understood that the heated portion of the porous membrane was not integrated.

Example 8

[Production of Cellulose Acetate Porous Membrane]
(Preparation of Dope)
A dope having the following composition was prepared.
Specifically, cellulose acetate was dissolved in dimethyl chloride, and methanol was added to the solution little by little. Next, glycerin and pure water were added to the solution little by little to obtain a solution with almost no undissolved material, and the solution was filtered with a filter paper. Thereby, a dope was prepared.
Dope Composition
5 parts by mass of cellulose acetate (degree of substitution 2.9)
0.2 parts by mass of glycerin
55 parts by mass of dimethyl chloride
34 parts by mass of methanol
6 parts by mass of pure water
(Production of Porous Membrane)
The prepared dope was sent by a gear pump, was filtered, and then was flow-cast from a die on a polyethylene terephthalate (PET) film which was transported on an endless band.
The flow-cast membrane was dried with a dry air at 20° C. to 40° C. for 20 minutes.
The dried flow-cast membrane was peeled off together with the PET film from the endless band, was dried with hot air at 80° C. to 120° C. for 15 minutes, and was wound with a winder. A number of fine pores was formed in the cellulose acetate on PET.
A cellulose acetate porous membrane was peeled off from the PET film using a peeling bar.
[Production of Chamber for Transplantation]
End portions were joined at 260° C. in the same procedures as in Example 1 such that a surface (a side opposite to a surface of the PET film side) of the produced membrane to which dry air was applied was an inner side. Thereby, a chamber for transplantation was produced.

Comparative Examples 1 to 3

[Production of Porous Membrane]
A porous membrane was produced by the same method as in Example 1.
[Production of Chamber for Transplantation]
The produced polysulfone porous membrane was cut into 3 cm×5 cm. The cut polysulfone porous membrane was folded into two such that a surface to which air was applied during the manufacture became an inner side, and the folded crease portion was cut with scissors. Thereafter, a 3 cm×5 cm polyethylene film (SUZURON L N-280, AICELLO CORPORATION) of which a center (1.8×0.8 cm) was hollowed out was inserted into the polysulfone porous membranes, and using a sealer for tea bag (T-230K) manufactured by FUJIIMPULSE CO., LTD., three sides of two long sides and one short side of a 3 cm×2.5 cm rectangle were joined by heating them at the temperature shown in the table, and thereby a bag shape in which an unjoined portion at the center was 1.0 cm×2.0 cm was obtained. The temperature was measured by a thermocouple. Thereafter, the remaining one side was inserted in a state where a metal rod was inserted into Intramedic polyethylene tube (PE200), and in this state, both were respectively heated at the same temperature using the same sealer. Thereafter, a peripheral portion was cut off such that a joint portion had the width shown in Table 1. Thereby, a chamber for transplantation was produced.

Comparative Examples 4 to 6

[Production of Chamber for Transplantation]
A biopore (BGCM00010) manufactured by Millipore was cut into 3 cm×5 cm. The cut biopore was folded into two such that a surface to which air was applied during the manufacture became an inner side, and the folded crease portion was cut with scissors. Thereafter, a 3 cm×5 cm polyethylene film (SUZURON L N-280, AICELLO CORPORATION) of which a center (1.8×0.8 cm) was hollowed out was inserted into the biopores, and using a sealer for tea bag (T-230K) manufactured by FUJIIMPULSE CO., LTD., three sides of two long sides and one short side of a 3 cm×2.5 cm rectangle were heated at the temperature shown in the table, and thereby a bag shape in which a portion of the center, which was not welded, was 1.0×2.0 cm was obtained. The temperature was measured by a thermocouple. Thereafter, the remaining one side was inserted in a state where a metal rod was inserted into Intramedic polyethylene tube (PE200), and in this state, both were respectively heated at the same temperature using the same sealer. Thereafter, a peripheral portion was cut off such that a joint portion had the width of the table. Thereby, a chamber for transplantation was produced.

<Evaluation of Chamber for Transplantation>
The chambers for transplantation were evaluated according to the following items. The results are shown in Table 1.
[Porosity]
Cross-section cutting was performed on a randomly selected joint portion using a freezing microtome (−160° C.), and the cross-section sample was subjected to conductive treatment (approximately 10 nm of a thickness of osmium coated film). Thereafter, SEM imaging (SU8030 type FE-SEM manufactured by Hitachi High-Technologies Corporation, acceleration voltage: 2 kV) was performed, a portion (observation width 500 pin) in which vacancies were observed in the cross-sectional SEM image was traced using a digitizer, and a porosity was quantified and evaluated according to the following criteria:
(A) 5% or less;
(B) more than 5% and 20% or less; and
(C) more than 20%.
[Integrity]
An integrity test kit for small volume devices (catalog number SLTEST000) manufactured by Millipore was attached to a port of the chamber for transplantation. Thereafter, the chamber was immersed in ethanol, air was injected into the chamber using a syringe, and the chamber was determined to have no defects in a case where a pressure could be applied to 0.3 kg/cm$^2$. Evaluation was performed according to the following criteria by the number of chambers not having defects in the integrity test using air injection/10 tests.

(A) 10 chambers
(B) 8 chambers or 9 chambers
(C) 7 chambers or less

[Glucose Responsiveness]

A glucose responsiveness was evaluated by the following procedures.

(1) Pancreatic islets (manufactured by COSMO BIO, mouse origin, same day use) were transferred from a tube to a petri dish with a micropipette, and preculture was performed for 1 to 2 hours.

(2) The produced chamber for transplantation was immersed in a culture medium (PNIM3 manufactured by COSMO BIO) in another petri dish, and the petri dish was evacuated for 10 minutes with a vacuum pump.

(3) Pancreatic islets in the petri dish were counted using a microscope (5 to 30 numbers), were adjusted in the culture medium such that the total volume became 100 μL, and were inserted into the chamber for transplantation.

(4) The tube was heat-sealed and joined. Thereby, a device for transplantation was obtained.

(5) The obtained device for transplantation was immersed in 3 mL of a medium containing 3 mM glucose in a petri dish, and was left to stand in an incubator at 37° C. for 60 minutes in the presence of 5% of $CO_2$.

(6) The medium containing 3 mM glucose in the petri dish was removed, 3 mL of a medium containing 3 mM glucose was newly added, and the device for transplantation was left to stand in an incubator at 37° C. for 60 minutes in the presence of 5% of $CO_2$.

(7) The device for transplantation left to stand for 60 minutes was taken out, and a medium outside the device for transplantation was recovered (the recovered medium was defined as 3 mM/60-120 min fraction).

(8) 3 mL of a medium containing 20 mM glucose was newly added to the petri dish, and the device for transplantation was left to stand in an incubator at 37° C. for 60 minutes in the presence of 5% of $CO_2$.

(9) The device for transplantation left to stand for 60 minutes was taken out, and a medium outside the device for transplantation was recovered in a 1.5 mL tube (the recovered medium was defined as 20 mM/0-60 min fraction).

(10) An amount of insulin in the 3 mM/60-120 min fraction and the 20 mM/0-60 min fraction was quantified, the following SI value was calculated, and evaluation was performed according to the following criteria.

$SI$=(Insulin concentration of 20 mM/0-60 min fraction)÷(Insulin concentration of 3 mM/60-120 min fraction)

(A) 1.8 or more
(B) 1.3 or more and less than 1.8
(C) less than 1.3

TABLE 1

| | Composition | Whether organic porous membranes are integrated with each other | Temperature (° C.) | Sealing width (mm) | Orientation of compact layer | Porosity (%) | | Integrity | | Glucose responsiveness (SI value) | |
|---|---|---|---|---|---|---|---|---|---|---|---|
| Example 1 | PSf/PSf | Integrated | 230 | 1.1 | Inside/inside | 2 | A | 10 | A | 2.1 | A |
| Example 2 | PSf/PSf | Integrated | 260 | 1.1 | Inside/inside | 1 | A | 10 | A | 2.3 | A |
| Example 3 | PSf/PSf | Integrated | 230 | 0.9 | Inside/inside | 2 | A | 10 | A | 2.0 | A |
| Example 4 | PSf/PSf | Integrated | 230 | 0.7 | Inside/inside | 2 | A | 10 | A | 2.1 | A |
| Example 5 | PSf/PSf | Integrated | 230 | 0.5 | Inside/inside | 2 | A | 10 | A | 2.4 | A |
| Example 6 | PSf/PSf | Integrated | 230 | 0.9 | Outside/inside | 2 | A | 10 | A | 1.9 | A |
| Example 7 | PSf/PSf | Integrated | 230 | 0.9 | Outside/outside | 2 | A | 10 | A | 1.4 | B |
| Example 8 | CA/CA | Integrated | 260 | 0.9 | Not orientated | 1 | A | 9 | B | 2.1 | A |
| Comparative Example 1 | PSf/Polyethylene/PSf | Not integrated | 230 | 1.3 | Inside/inside | 4 | A | 9 | B | 1.1 | C |
| Comparative Example 2 | PSf/Polyethylene/PSf | Not integrated | 230 | 1.1 | Inside/inside | 4 | A | 5 | B | 1.0 | C |
| Comparative Example 3 | PSf/Polyethylene/PSf | Not integrated | 230 | 0.9 | Inside/inside | 4 | A | 3 | C | 1.1 | C |
| Comparative Example 4 | PTFE/Polyethylene/PTFE | Not integrated | 230 | 1.3 | No compact layer | 4 | A | 10 | A | 1.1 | C |
| Comparative Example 5 | PTFE/Polyethylene/PTFE | Not integrated | 230 | 1.1 | No compact layer | 4 | A | 10 | A | 1.2 | C |
| Comparative Example 6 | PTFE/Polyethylene/PTFE | Not integrated | 230 | 0.9 | No compact layer | 4 | A | 3 | C | 1.0 | C |
| Comparative Example 7 | PSf/PSf | | 180 | 1.1 | Inside/inside | 52 | C | 8 | B | 2.1 | A |

EXPLANATION OF REFERENCES

1: Chamber for transplantation
2: Porous membrane
3: Joint portion
100: Thermoplastic resin layer

What is claimed is:

1. A chamber for transplantation, comprising:
one or more membranes for immunoisolation at a boundary between an inside and an outside of the chamber for transplantation,
wherein all of the membranes for immunoisolation include a porous membrane containing a polymer, and
a joint portion at which end portions of one porous membrane or end portions of two porous membranes are directly fusion welded to each other is provided, and
wherein the porous membrane has, in an inside thereof, a layered compact portion where a pore diameter is the smallest.

2. The chamber for transplantation according to claim 1, wherein different end portions of one porous membrane are directly fusion welded to each other at the joint portion.

3. The chamber for transplantation according to claim 1, wherein end portions of two porous membranes are directly fusion welded to each other at the joint portion.

4. The chamber for transplantation according to claim 1, wherein a width of the joint portion is 0.1 mm to 1.5 mm.

5. The chamber for transplantation according to claim 1, wherein all of the porous membranes contain polysulfone or polyethersulfone.

6. The chamber for transplantation according to claim 1, wherein the pore diameter continuously increases in a thickness direction from the compact portion toward at least one surface of the porous membrane.

7. The chamber for transplantation according to claim 1, wherein the compact portion is present close to any one surface X from a central portion in thickness of the porous membrane.

8. The chamber for transplantation according to claim 7, wherein the surface X is on the inside.

9. A device for transplantation, comprising the chamber for transplantation according to claim 1 enclosing a biological constituent therein.

10. The device for transplantation according to claim 9, wherein the biological constituent releases a physiologically active substance.

11. The device for transplantation according to claim 10, wherein the physiologically active substance is insulin.

12. A method for transplanting a biological constituent into a recipient, comprising enclosing a biological constituent in the chamber for transplantation according to claim 1.

13. A method for preventing an immune rejection by a recipient in a case of transplantation, comprising enclosing a biological constituent in the chamber for transplantation according to claim 1.

14. A method for manufacturing a chamber for transplantation having one or more membranes for immunoisolation at a boundary between an inside and an outside,
    wherein all of the membranes for immunoisolation include a porous membrane containing a polymer, and
    the method comprising: directly fusion welding end portions of one porous membrane to each other or directly fusion welding end portions of two porous membranes to each other, and wherein the porous membrane has, in an inside thereof, a layered compact portion where a pore diameter is the smallest.

15. A method for manufacturing a chamber for transplantation according to claim 14, the method comprising:
    preparing one or more porous membranes containing a polymer selected from polysulfone and polyethersulfone;
    bringing one part of the porous membrane into direct contact with another part of the porous membrane; and
    performing a heat fusion welding of the two parts that are in direct contact with each other at a temperature which is a glass transition temperature of the polymer or higher and lower than a melting point of the polymer.

16. The manufacturing method according to claim 15, wherein the heat fusion welding is performed at 230° or higher and lower than 340° C.

17. The manufacturing method according to claim 15, further comprising, bringing different end portions of one porous membrane into direct contact with each other.

18. The manufacturing method according to claim 15, further comprising, bringing end portions of two porous membranes into direct contact with each other.

19. The manufacturing method according to claim 16, further comprising, bringing different end portions of one porous membrane into direct contact with each other.

* * * * *